United States Patent
Sitther et al.

(10) Patent No.: US 11,162,067 B2
(45) Date of Patent: Nov. 2, 2021

(54) COMPOSITION AND METHOD FOR ENHANCING PHOTOSYNTHETIC EFFICIENCY OF MICROORGANISMS

(71) Applicant: Morgan State University, Baltimore, MD (US)

(72) Inventors: Viji Sitther, Pikesville, MD (US); Kadir Aslan, Baltimore, MD (US); Behnam Tabatabai, Middle River, MD (US)

(73) Assignee: Morgan State University, Baltimore, MD (US)

( * ) Notice: Subject to any disclaimer, the term of this patent is extended or adjusted under 35 U.S.C. 154(b) by 343 days.

(21) Appl. No.: 15/678,643

(22) Filed: Aug. 16, 2017

(65) Prior Publication Data

US 2018/0051246 A1 Feb. 22, 2018

Related U.S. Application Data

(60) Provisional application No. 62/375,498, filed on Aug. 16, 2016.

(51) Int. Cl.

| | |
|---|---|
| *C12N 1/38* | (2006.01) |
| *C12P 7/64* | (2006.01) |
| *C12N 1/20* | (2006.01) |
| *C12P 9/00* | (2006.01) |
| *C12P 33/00* | (2006.01) |
| *C12P 23/00* | (2006.01) |
| *C10L 1/02* | (2006.01) |
| *C12N 1/12* | (2006.01) |

(52) U.S. Cl.
CPC .............. *C12N 1/38* (2013.01); *C10L 1/02* (2013.01); *C12N 1/12* (2013.01); *C12N 1/20* (2013.01); *C12P 7/64* (2013.01); *C12P 7/6445* (2013.01); *C12P 9/00* (2013.01); *C12P 23/00* (2013.01); *C12P 33/00* (2013.01); *C10L 2200/0469* (2013.01); *C10L 2290/26* (2013.01)

(58) Field of Classification Search
None
See application file for complete search history.

(56) References Cited

PUBLICATIONS

Schrofel et al., Biosynthesis of gold nanoparticles using diatoms—silica-gold and EPS-gold bionanocomposite formation, Journal of Nanoparticle Research, 2011, vol. 13, No. 8, p. 3207-3216.*

Lengke et al., Morphology of Gold Nanopartcles Synthesized by Filamentous Cyanobacteria from Gold(I)-Thiosulfate and Gold(III)-Chloride Complexes, Langmuir 2006, 22, 2780-2787.*

Joutey et al., Biodegradation: Involved Microorganisms and Genetically Engineered Microorganisms, Biodegradation—Life of Science—Chapter 11 (2013).*

(Continued)

*Primary Examiner* — Erin M. Bowers
(74) *Attorney, Agent, or Firm* — Whiteford, Taylor & Preston, LLP; Peter J. Davis

(57) ABSTRACT

Compositions including metal nano- and/or micro-particles in solution with photosynthetic bioproduct producing microorganisms. These light harvesting complexes increase growth rates and photosynthetic efficiency of the constituent microorganisms, reducing the light required for a specific production level, or increases production for a specific light level.

18 Claims, 3 Drawing Sheets

(56) References Cited

PUBLICATIONS

Singh et al., Distinct salt-dependent effects impair Fremyella diplosiphon pigmentation and cellular shape, Plant Signalling & Behavior, 8:7, e24713; Jul. 2013.*

Tabatabai et al., Plant Posters, p. 2000, 2014 World Forum on Biology Abstract Issue.*

Sayanova et al., Modulation of lipid biosyhtesis by stress in diatoms, Phil. Trans. R. Soc. B 372: Apr. 7, 2016 (2017).*

Lengke et al., Langmuir 22: 2780-2787 (2006).*

* cited by examiner

COMPOSITION AND METHOD FOR ENHANCING PHOTOSYNTHETIC EFFICIENCY OF MICROORGANISMS

FIELD OF THE INVENTION

The present invention relates to compositions and methods for increasing the photosynthetic capacity of microorganisms.

DESCRIPTION OF THE BACKGROUND

The need and the market for microorganism propagation technology has expanded dramatically in the last decades with more and more "bioproducts" being produced experimentally and even commercially using specially engineered microorganisms. One important class of bioproducts is lipids. Lipids are naturally occurring molecules that include fats, waxes, sterols, fat-soluble vitamins (such as vitamins A, D, E, and K), monoglycerides, diglycerides, triglycerides, phospholipids, and others. Lipids are typically contained in photosynthetic bacteria and algae in the form of membrane components, storage products, and metabolites. Certain algal strains, particularly microalgae such as diatoms, certain chlorophyte species, and bacteria such as cyanobacteria, contain proportionally high levels of lipids. Algal sources for the algae oils can contain varying amounts, e.g., from 2 wt % to 40 wt % of lipids, based on total weight of the biomass itself.

Other bioproducts include biopolymers, nutraceuticals (e.g., vitamins) and pharmaceuticals; such as antimicrobials, antivirals, antifungals, neuroprotectives.

Another bioproduct is "biofuel," which includes fuel derived from biomass conversion. This renewable source of energy significantly contributes to energy security and alleviates the harmful effects of particulates, carbon monoxide and hydrocarbons in diesel-powered vehicles. With the negative impact of fossil fuel on the environment, it is more important than ever to find alternative sources of energy. Biofuel derived from cyanobacteria and algae has replaced around 1 billion gallons of petroleum diesel. The U.S. Department of Energy estimates that oil yields from cyanobacteria/algae range from 1,000-6,500 gallons/acre/year. Calculation and analysis of oil from lipids indicates a theoretical yield of 38,000 gallons/acre/year and a current practical yield of 4,350-5,700 gallons/acre/year from cyanobacteria/algae. These organisms convert light energy into chemical energy through photosynthesis. Since cyanobacteria provide very high levels of net energy, converting biomass into fuel is much less energy-intensive than other methods of conversion.

A recent analysis showed that current water and land resources in the U.S. could support the production of as much as 23.5 billion gallons/year (BGY) of algae-based fuel. The study also projected the number could be increased by 78.2 BGY (or 2.5 billion barrels/year) from biofuel production in saline waters. The U.S. Navy alone uses 36.5 million barrels of oil per year. It has mandated that 50% of its energy needs will be from domestic renewable fuel by 2020 as part of its national security strategy and it is investing heavily in the biofuel industry. The biofuel industry is expanding and is expected to double over the next 10 years into a $185 billion industry.

*F. diplosiphon* has great potential as a production-scale biofuel agent. With a fast regeneration time and capability to grow in low light intensity as low as 15 µmol quanta $m^{-2}s^{-1}$ and an optimal temperature of 28° C., it used as a model organism used to study photosynthesis. A light-dependent acclimation process known as complementary chromatic adaptation (CCA), enables the organism to absorb light and grow in a range of environmental conditions. CCA allows this species to live at various depths of the ocean, despite varying intensities of light. While several aspects of its growth in various wavelengths of light have been studied, there has been no attempt to enhance its photosynthetic potential using nanotechnology.

Recently, the inventors genetically transformed the wild type strain of *F. diplosiphon* for enhanced halotolerance. The transformant is described in U.S. application Ser. No. 14/873,879, the entirety of which is incorporated herein by reference. The halotolerant strain is now capable growing in marine water with an average concentration of 35 g/L NaCl.

SUMMARY OF THE INVENTION

The present invention arises from the discovery by the inventors that nano- and micro-particles, when complexed to bioproduct-producing and biomass/biofuel photosynthetic microorganisms, can increase both the growth rate and the photosynthetic efficiency of the microorganism, as compared to non-complexed microorganisms. Accordingly, the artificial light harvesting complexes of the invention reduces the amount of artificial light (and associated costs) required for a certain bioreactor growth rate and/or increase the production capacity of a bioreactor without increasing costs.

Accordingly, there is presented according to the invention a composition including a nano- and/or micro-particle complexed to a photosynthetic organism.

According to various embodiments of the invention, the particles of the complex may be metal particles, such as gold, silver, copper, and silicon, and microorganisms of the complex may be bacteria, algae, chlorophyte, protists, and fungi.

According to further embodiments of the invention, the photosynthetic bacteria may be selected from the group consisting of *F. diplosiphon, Nostoc* sp., *Tolypothrix* sp., *Calothrix* sp., *Synechococcus elongatus, Synechocystis* sp. PCC6803, *Arthrospira* sp., *Aphanothece* sp., and *Anabaena* sp.

According to a preferred embodiment of the invention, the microorganism may be *F. diplosiphon*.

According to a further preferred embodiment of the invention, the microorganism may be a strain of *F. diplosiphon* that has increased halotolerance relative to wild type strains.

According to a further preferred embodiment of the invention, the particle may be a gold nano-particle (also referred to as "GNP" and "AuNP").

According to still further embodiments of the invention, the photosynthetic algae may be selected from the group consisting of diatoms, *Chlorella* sp., *Nannochloris* sp., and *Dunaliella tertiolecta*.

According to still further embodiments of the invention, the microorganism may be suitable for use as a biofuel.

According to other embodiments of the invention, the microorganism may be a bioproduct producing microorganism. According to various sub-embodiments, the microorganism may produce lipids selected from the group consisting of fats, waxes, sterols, fat-soluble vitamins (such as vitamins A, D, E, and K), monoglycerides, diglycerides, triglycerides, and phospholipids.

According to further embodiments of the invention, the microorganism may produce bioproducts selected from the group consisting of biopolymers, nutraceuticals and pharmaceuticals, wherein the pharmaceuticals include antimicrobials, antivirals, antifungals, and neuroprotectives.

According to various embodiments of the invention, the particle may be a nano-particle having a size of 20-100 nm. According to various other embodiments, the particle may be a micro-particle having a size of 100-200 nm. According to still further embodiments, the composition may include both nano- and micro-particles complexed to a photosynthetic organism.

According to various further embodiments of the invention, the nano- and/or micro-particles of the invention may have any shape, including spheres, rods, fibers, films, wires, and tubes.

According to further embodiments of the invention, the relative concentration of nano- and/or micro-particles to microorganism cells may be 1:4, 1:2, 1:1, 2:1, or 4:1.

According to a most preferred embodiment, the composition may include a gold nano-particle of 200 nm complexed to *F. diplosiphon* cells in a ratio of 1:1.

According to further embodiments, various surface modifications can provide a stronger attachment of the nano-particle to the cell surface, further enhancing light capture and scatter, and hence photosynthetic pigment accumulation, lipid and other bio-product production.

According to further embodiments of the invention, the nano-particle-photosynthetic microorganism complexes of the invention may be grown in bioreactors having an artificial light source with specific and predetermined light wavelengths and/or light pulsations tuned to the absorbance profile of the complexes to increase microorganism growth and production of desired bioproducts.

According to other embodiments of the invention, the nano-particle-photosynthetic microorganism complexes of the invention may be used in batch, batch-fed, recycling, fluidized bed and/or hollow-fiber bioreactors to increase the efficacy of photosynthesis for the production of the resulting bioproducts.

DETAILED DESCRIPTION

Figure 1:
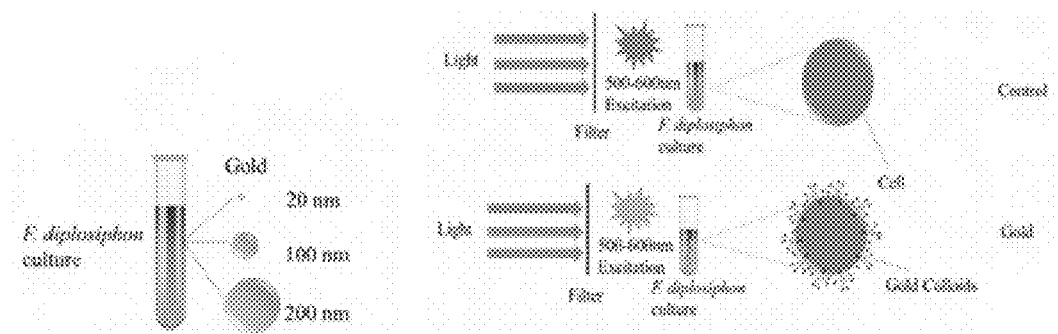
FIG. 1 is a representation of selected experiments that were used to demonstrate aspects of the invention.
Figure 2:
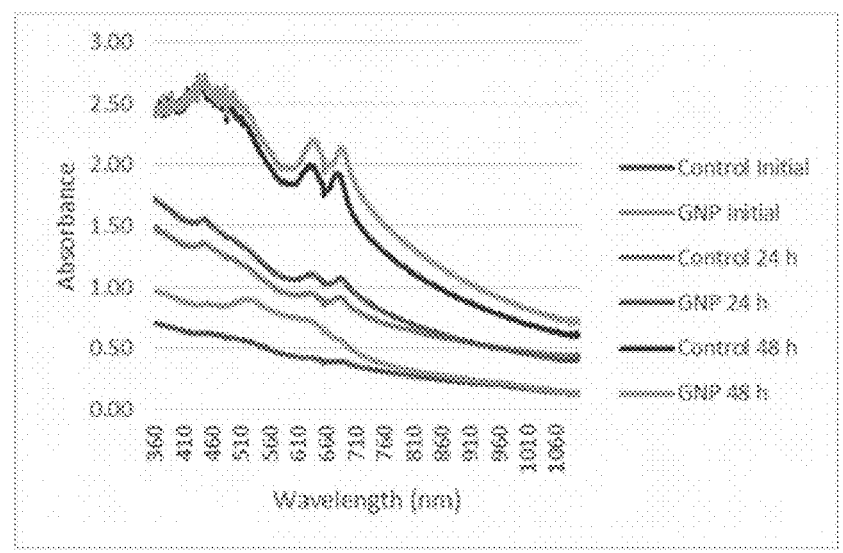
FIG. 2 is a line graph showing absorbance versus wavelength for *F. diplosiphon* cells loaded with gold nano-particles ("GNP").

The inventors have developed artificial light harvesting complexes in *F. diplosiphon* using gold nano-particles, taking advantage of the discovery that the wavelengths of light at which gold nano-particles are excited correspond to the wavelengths of light that are utilized by *F. diplosiphon* for photosynthesis. FIG. 1 shows a graphic depiction of experiments conducted by the inventors in connection with the making of this invention, using gold nano-particles with *F. diplosiphon* cells. Gold nano-particles are non-toxic to the growth of *F. diplosiphon*, and FIG. 2 shows that the nano-cultures (gold nano-particles in solution with *F. diplosiphon* cells) have a faster growth rate than *F. diplosiphon* non-complexed cell cultures. More specifically, FIG. 2 shows that a 1:1 ratio of 20 nm gold nano-particles to *F. diplosiphon* cells produces enhanced spectral absorbance at wavelengths corresponding to chlorophyll a and phycobiliproteins as well as at 750 nm (orange and blue lines), indicating an increase in photosynthetic pigment accumulation after 48 hrs.

Figure 3:
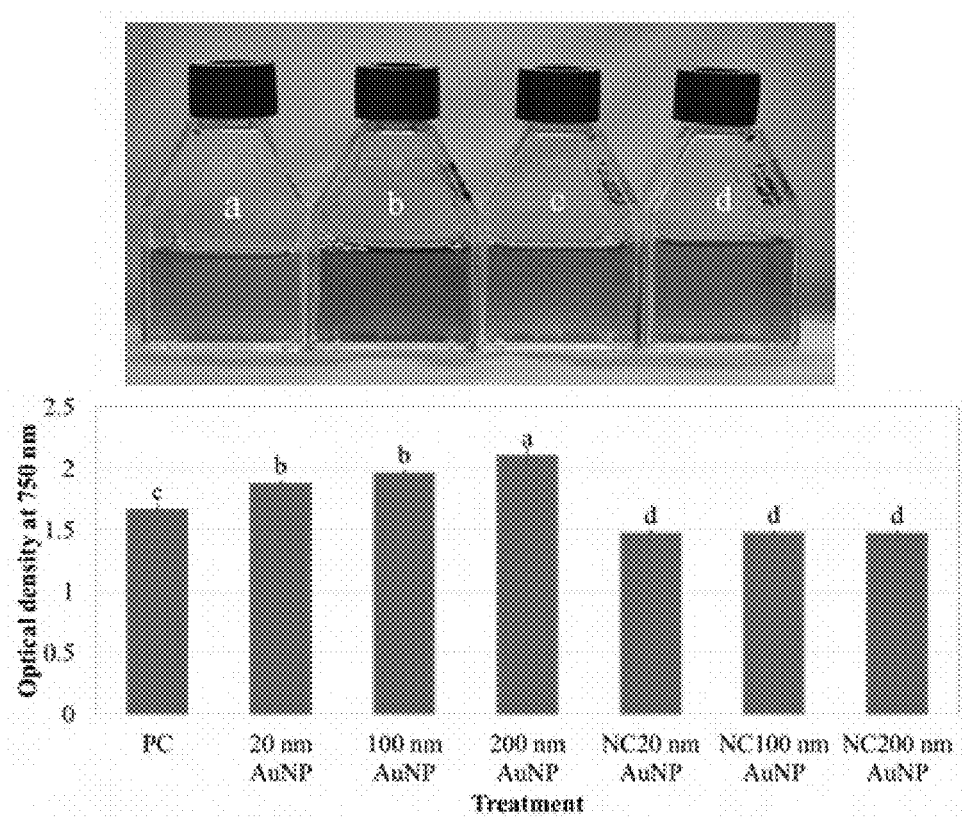
FIG. 3 shows culture flasks containing *F. diplosiphon* cells loaded with different size gold-nano-particles ("AuNP") (top) and a bar graph showing optical densities at 750 nm for those cultures (bottom).

Additionally, cultures of *F. diplosiphon* exposed to gold nano-particles exhibited higher optical densities at 750 nm ($OD_{750}$), which is commonly used to measure culture growth since changes in pigmentation will not interfere with absorbance at this wavelength. Referring to FIG. 3, *F. diplosiphon* was cultivated in culture flasks without nano-particles (flask a), and in solution with 20 nm (flask b), 100 nm (flask c), and 200 nm (flask d) gold colloids, see top of FIG. 3. After nine days, a significant increase in *F. diplosiphon* growth (measured by $OD_{750}$) was observed in cultures treated with 20, 100, and 200 nm gold nano-particles with maximum increase in growth observed in cultures treated with 200 nm gold nano-particles ("AuNPs"), see data bottom of FIG. 3. Cells grown in the absence of gold nano-particles served as positive control (PC) and gold colloids alone served as negative controls (NC).

Figure 4:
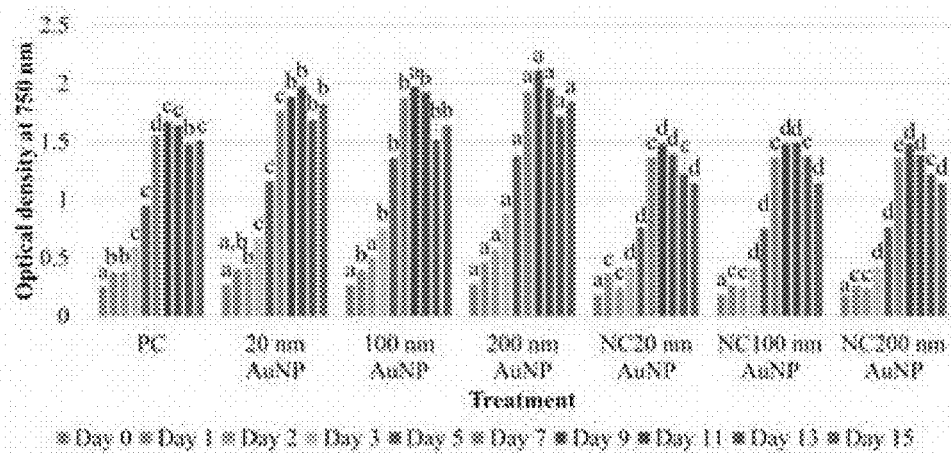
FIG. 4 is a bar graph showing optical densities at 750 nm for cultures of *F. diplosiphon* cells loaded with different size gold nano-particles ("AuNP") over time.

In addition, impact of 20, 100, and 200 nm-diameter AuNPs on *F. diplosiphon* growth was determined by measuring $OD_{750}$ over a period of 15 days. Cells grown in the absence of AuNPs served as positive control (PC) and AuNP suspensions served as negative controls (NC). While all other treatments achieved peak growth by the ninth day, cultures in solution with 20 nm AuNPs exhibited prolonged growth to 11 days (FIG. 4).

Figure 5:
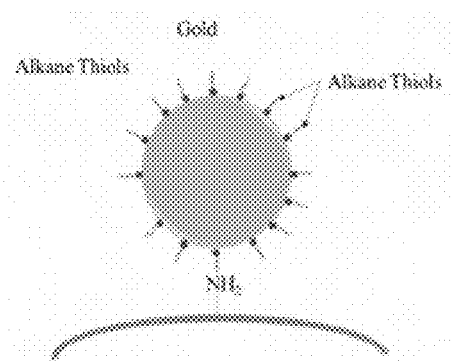
FIG. 5 is a representation of a surface-modified gold nano-particle complexed to a photosynthetic microorganism.

FIG. 5 shows self-assembled monolayers of alkane thiols binding to the surface of the AuNPs to enhance photosynthesis of a complexed microorganism. Such surface modifications can provide a stronger attachment of the nanoparticle to the cell surface, further enhancing light capture and scatter, and hence photosynthetic pigment accumulation, lipid and other bio-product production.

The invention claimed is:

1. A composition comprising a gold nano-particle complexed to a strain of *F. diplosiphon* having increased halotolerance relative to wild type strains of *F. diplosiphon*.

2. A composition according to claim 1, wherein the strain of *F. diplosiphon* having increased halotolerance relative to wild type strains of *F. diplosiphon* is suitable for use as a biofuel.

3. A composition according to claim 1, wherein the strain of *F. diplosiphon* having increased halotolerance relative to wild type strains of *F. diplosiphon* is a bioproduct producing microorganism.

4. A composition according to claim 3, wherein the strain of *F. diplosiphon* having increased halotolerance relative to wild type strains of *F. diplosiphon* produces a lipid selected from the group consisting of fats, waxes, sterols, fat-soluble vitamins, monoglycerides, diglycerides, triglycerides, and phospholipids.

5. A composition according to claim 3 wherein the strain of *F. diplosiphon* having increased halotolerance relative to wild type strains of *F. diplosiphon* produces a bioproduct selected from the group consisting of biopolymers, nutraceuticals and pharmaceuticals.

6. A composition according to claim 1, wherein the gold nano-particle is a nano-particle having a size of 20-100 nm.

7. A composition according to claim 1, wherein the gold nano-particle is a micro-particle having a size of 100-200 nm.

8. A composition according to claim 1, wherein the composition comprises both gold nano-particles complexed to said strain of *F. diplosiphon* having increased halotolerance relative to wild type strains of *F. diplosiphon*.

9. A composition according to claim 1, wherein the nano-particles have a shape selected from the group consisting of spheres, rods, fibers, films, wires, and tubes.

10. A composition according to claim 1 wherein the relative concentration of gold nano-micro-particles to cells of *F. diplosiphon* having increased halotolerance relative to wild type strains of *F. diplosiphon* is selected from the group consisting of 1:4, 1:2, 1:1, 2:1, and 4:1.

11. A composition according to claim 1, wherein in said composition comprises a gold nano-particle of 200 nm complexed to *F. diplosiphon* cells having increased halotolerance relative to wild type strains of *F. diplosiphon* in a ratio of 1:1.

12. A method for producing biofuels comprising growing the compositions according claim 1 in a bioreactor with an artificial light source having a specific and predetermined light wavelengths and/or light pulsations tuned to the absorbance profile of said compositions to increase microorganism growth and production of desired bioproducts.

13. A method according to claim 12, wherein said bioreactor is selected from the group consisting of batch, batch-fed, recycling, fluidized bed and/or hollow-fiber bioreactors.

14. A composition according to claim 1, wherein said composition has a faster growth rate than *F. diplosiphon* cells in the absence of gold nano-particles.

15. A composition according to claim 1, wherein said composition exhibits higher photosynthetic activity than *F. diplosiphon* cells in the absence of gold nano-particles.

16. A composition according to claim 1, wherein said composition exhibits enhanced spectral absorbance at wavelengths corresponding to Chlorophyll a than *F. diplosiphon* cells in the absence of gold nano-particles.

17. A composition according to claim 1, wherein said composition exhibits higher optical densities at 750 nm than native *F. diplosiphon* cells in the absence of gold nano-particles.

18. A composition according to claim 1, wherein said gold nano-particles comprise surface modifications that increase the strength of attachment of the gold nano-particles to cell surfaces of said *F. diplosiphon* having increased halotolerance relative to wild type strains of *F. diplosiphon*.

* * * * *